United States Patent [19]

Tanaka et al.

[11]   4,456,686
[45]   Jun. 26, 1984

[54] ANTIBIOTIC PA-39504-X₁ AND PRODUCTION THEREOF

[75] Inventors: Kentaro Tanaka; Eiji Kondo; Kouichi Matsumoto; Jun'ichi Shoji, all of Osaka; Naoki Tsuji, Hyogo, all of Japan

[73] Assignee: Shionogi & Co., Ltd., Osaka, Japan

[21] Appl. No.: 421,580

[22] Filed: Sep. 22, 1982

Related U.S. Application Data

[62] Division of Ser. No. 211,715, Dec. 1, 1980, Pat. No. 4,362,665.

[30] Foreign Application Priority Data

Dec. 12, 1979 [JP]   Japan ............................... 54-161170

[51] Int. Cl.³ .................. C12P 17/18; C12R 1/465
[52] U.S. Cl. ................................... 435/119; 435/886
[58] Field of Search .............................. 435/119, 886

[56] References Cited

U.S. PATENT DOCUMENTS 4,229,534  10/1980  Kahan et al. ..................... 435/119
4,235,967  11/1980  Cassidy et al. ..................... 435/119

Primary Examiner—Alvin E. Tanenholtz
Attorney, Agent, or Firm—Wenderoth, Lind & Ponack

[57] ABSTRACT

A new antibiotic having β-lactamase inhibitory activity, PA-39504-X₁ of the formula:

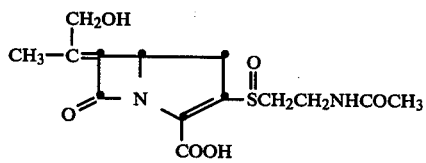

being useful as a medicament and a veterinary drug for inhibiting the growth of gram-positive and gram-negative pathogenic microorganisms and a process for preparing the same, being characterized by cultivating Streptomyces argenteolus PA-39504 or Streptomyces tokunonensis PA-31088 in a suitable medium and recovering PA-39504-X₁ from the cultured broth.

4 Claims, No Drawings

ANTIBIOTIC PA-39504-X₁ AND PRODUCTION THEREOF

This application is a division of application Ser. No. 211,715, filed Dec. 1, 1980 (now U.S. Pat. No. 4,362,665).

This invention relates to a new antibiotic, PA-39504-$X_1$ and the process for preparing the same by cultivating a strain of *Streptomyces argenteolus* in a suitable medium and recovering PA-39504-$X_1$ from the cultured broth.

Said new antibiotic PA-39504-$X_1$ inhibits the growth of both gram-positive and gram-negative pathogenic microorganisms. Furthermore, it shows a wide range of β-lactamase inhibitory activity.

The antibiotic PA-39504-$X_1$ has the following physicochemical properties.

(a) Mass spectrum of the methyl ester:
m/e: 341 [M+H−16]

(b) Circular dichroism spectrum (in water):
λ(nm) [θ]360 (0), 320 (−560), 267 (−6410), 245 (0), 240 (+1490), 230 (0), 220 (−2300), 210 (0).

(c) Ultraviolet absorption spectrum (in 0.1 M phosphate buffer solution (pH 7.0)):
$\lambda_{max}^{H2O}$ 240, 318 nm (d) NMR spectrum (in D₂O at 5° C.):
$\delta_{ppm}^{D2O}$ 2.29, 3.4–3.6, 3.8–4.0, 4.57, 5.4.

From the above data and other experimental results, the antibiotic PA-39504-$X_1$ is identified to be 3-[(2-acetamidoethyl)sulfinyl]-6-(1-hydroxymethylethylidene)-7-oxo-1-azabicyclo[3,2,0]hept-2-ene-2-carboxylic acid, the chemical structure of which is as follows:

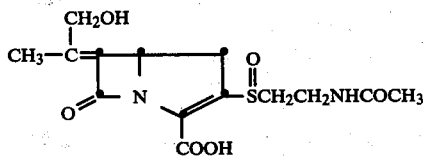

Various epithienamycins and olivanic acids with β-lactamase inhibitory activity are known (The Journal of Antibiotics 32, 961–963 (1979)). However, PA-39504-$X_1$ is different from those antibiotics in the structure, namely in the possession of 1-hydroxymethylethylidene at the 6 position of 7-oxo-1-azabicyclo[3.2.0]hept-2-ene. Accordingly, it is concluded that PA-39504-$X_1$ is a new antibiotic belonging to thienamycin antibiotics.

The antibiotic PA-39504-$X_1$ has the following biological properties:

(a) Anti-bacterial activity:

| Test Bacteria | Minimum Inhibitory Concentration (µg/ml) |
|---|---|
| *Staphylococcus aureus* 209P JC-1 | 6.25 |
| *Streptococcus pneumoniae* I | 0.78 |
| *Escherichia coli* NIHJ JC-2 | 3.13 |
| *Klebsiella pneumoniae* SRL-1 | 6.25 |
| *Klebsiella* sp. 363 (R) | 12.5 |
| *Proteus mirabilis* PR-4 | 6.25 |
| *Enterobactor cloacae* 233 | 12.5 |

Note: inoculum size 10⁶

(b) β-Lactamase inhibitory activity

| β-Lactamase Producing Bacteria | Minimum Inhibitory Concentration (µg/ml) |
|---|---|
| 1. Cephalosporinase producing *Enterobacter cloacae* 92 | 0.5 |
| 2. Penicillinase producing *Klebsiella* sp. 363 | 0.125 |

The antibiotic PA-39504-$X_1$ is produced by a microorganism belonging to the genus Streptomyces. A microorganism was isolated from a soil sample and tentatively named Streptomyces sp. strain No. PA-39504. The microorganism has been deposited in the Fermentation Research Institute of Agency of Industrial Science & Technology, Yatabe-machi, Ibaragi Pref. Japan, 300–21 under the accession number FERM-P No. 5265 since Nov. 5, 1979 and in American Type Culture Collection, 12301 Parklawn Drive, Rockville, Md. 20852, U.S.A. under the accession number, ATCC No. 31589 since Dec. 4, 1979.

Furthermore, PA-39504-$X_1$ can be produced by *Streptomyces tokunonensis* PA-31088 of which characteristics are disclosed in Japanese Patent Publication (Not-examined) No. 55-136282 published on Oct. 23, 1980. The strain has been deposited in Fermentation Research Institute under the accession number FERM-P No. 4843 since Feb. 26, 1979 and in American Type Culture Collection under the accession number 31569 since Sept. 19, 1979.

The microorganism Streptomyces sp. strain No. PA-39504 has the following characteristics:

(a) Morphological Properties (cultured on Bennett's agar medium at 28° C. for 14 days)

The microorganism grows well on Bennett's agar medium and forms aerial hyphae abundantly. Aerial hyphae branch simply and the ends form loops or short spirals. The aerial hyphae on the medium are brownish gray and the substrate hyphae are pale yellowish brown. No soluble pigment is produced. The surface of the spore is smooth under electron microscopy and the spores are short cylindrical. Any of sporangium, flagellated spore or sclerotium is not observed. Split by fragmentation in substrate hyphae is not observed.

(b) Physiological properties

| | |
|---|---|
| Liquefaction of gelatin | Negative |
| Hydrolysis of starch | Positive |
| Tyrosinase reaction | Negative |
| Production of melanoid pigment | Negative |
| Peptonization of milk | Positive |
| Coagulation of milk | Negative |

(c) Utilization of sugars
Good growth: L-arabinose, D-xylose, D-glucose D-fructose, inositol, L-rhamnose
No growth: sucrose, raffinose, D-mannitol (d) Growth temperature
10° C.: fair growth but few aerial hyphae are formed.
28° C.: good growth with well formed aerial hyphae.
37° C.: no growth
45° C.: no growth From the above properties, it is clear that the strain PA-39504 belongs to the Genus Streptomyces. The properties were elucidated with the description in "The Actinomycetes" 2 (1961) by Waksman, "International Journal of Systematic Bacteriology" by Shirling and Gottlieb (International Streptomyces Project) 18 (1968), 19 (1969) and 22 (1972), "Bergey's Manual of Determinative Bacteriology" 8th edition (1974) and other published literature. It was concluded that the strain PA-39504 belongs to *Streptomyces argenteolus* and is designated *Streptomyces argenteolus* PA-39504. The strains PA-39504 and PA-31088 have been deposited in the Fermentation Research Institute and American Type Culture Collection as noted above. This invention includes all natural and artificial mutants and variants of both the above-described microorganisms as long as it produces PA-39504-$X_1$ and cannot be clearly distinguished from the above-described microorganisms. The artificial production of mutants may be accomplished by a conventional procedure such as X-ray or ultraviolet ray irradiation or treatment with nitrogen mustards, 4-nitroquinoline N-oxide, N-methyl-N'-nitro-N-nitrosoguanidine and other mutagens.

The production of PA-39504-$X_1$ is carried out by cultivating the PA-39504-$X_1$ producing strain in an enriched medium under aerobic conditions, whereupon PA-39504-$X_1$ is isolated from the cultured broth. A general method of preparing PA-39504-$X_1$ is as follows:

The conditions of fermentation and the composition of the medium follow the usual known procedure for producing antibiotics. The composition of the medium may be varied over a very wide range. It essentially consists of carbon sources, nitrogen sources and inorganic elements. Vitamins, precursors and other materials to stimulate the fermentation may be added, if necessary. Examples of suitable carbon sources are glucose, starch, dextrin, glycerol, molasses, organic acids and the like. They may be used singly or in combination. Examples of nitrogen sources are soybean meal, corn steep liquor, meat extract, yeast extract, cotton seed flour, peptone, wheat germ, ammonium sulfate and ammonium nitrate, which may be used singly or in combination. The inorganic elements may be selected from, for example, calcium carbonate, sodium chloride, potassium chloride, magnesium sulfate, cobalt chloride, various phosphates and the like. They are added to the medium if the occasion demands. Liquid media are preferred for production on a large scale.

Fermentation may be carried out under aerobic or submerged aerobic conditions. A submerged aerobic culture is preferable. The pH of the medium may be adjusted to about 5.5 to 8.5. A buffering agent such as calcium carbonate may be added to the medium if the pH of the medium varies during the fermentation.

The temperature may be kept at about 20° to 40° C., more preferably at about 25° to 32° C., during fermentation. The fermentation period depends on the scale. It takes about 20 to 80 hours on a large scale. If excessive foaming takes place during the fermentation, antifoaming agents such as vegetable oil, lard oil, and polypropylene glycol may be added to the medium prior to or in the course of fermentation.

The antibiotic PA-39504-$X_1$ can be isolated from fermentation broth in a per se conventional manner. There may be employed any conventional method such as filtration, centrifugation, adsorption and desorption with ion-exchange resins, chromatography with various active adsorbents, extraction with suitable solvents and the like. The procedures may be combined in appropriate order. During the isolation procedure, PA-39504-$X_1$ may be converted into the salt with a suitable base and a suitable stabilizing agent may be added in order to avoid the decomposition.

The antibiotic PA-39504-$X_1$ can be converted into the pharmaceutically acceptable salts for use as medicament and veterinary drug. There are exemplified sodium, potassium, calcium, barium salts and the like.

The abtibiotic PA-39504-$X_1$ is useful as a medicament, a veterinary drug, or as a sterilizer being effective against gram-positive and gram-negative bacteria including $\beta$-lactamase-producing strains. Therefore, PA-39504-$X_1$ and its pharmaceutically acceptable salts may be orally or parenterally administered to humans or animals. The antibiotic may be made into tablets, capsules, powder or the like in admixture with diluents, stabilizing agents, preservatives, detergents and the like for oral administration. Further, it may be administered in forms of an injection preparation, ointment or suppositories.

The dosage of PA-39504-$X_1$ is generally about 1/10th to several times that of cefalotin, although this is variable depending on the purpose of the treatment. For example, the daily dosage for a human adult is about 0.1 to about 30 g for a subcutaneous injection.

PA-39504-$X_1$ has a strong $\beta$-lactamase inhibitory activity and synergetically increases the anti-bacterial activity of known $\beta$-lactam type antibiotics against $\beta$-lactamase producing bacteria. Therefore, PA-39504-$X_1$ may be used in combination with the well-known antibiotics of the $\beta$-lactam type such as penicillins, e.g. benzylpenicillin, phenoxymethylpenicillin, carbenicillin, ampicillin, amoxicillin and the like, and cephalosporins, e.g. cefaloridine, cefalotin, cefazolin, cefalexin, cefacetrile, cefamandole, cefradine, cefaloglycin, cefoxitin, cefapirin and the like.

The following examples are given solely for the purpose of further explanation and is not to be construed as limiting of the present invention, many variations of which are possible.

EXAMPLE 1

(a) Fermentation process

Medium S-1: soluble starch 0.5%, glucose 0.5% polypeptone 0.5%, meat extract 0.5%, yeast extract 0.25%, sodium chloride 0.25%, and deionized water (pH 7.0 before sterilization).

A slant of seed culture of Streptomyces sp. PA-39504-$X_1$ (FERM-P No. 5265) is inoculated into a 2-liter Erlenmeyer flask containing 800 ml of Medium S-1 of the above composition and incubated at 28° C. for 48 hours under stirring at 180 r.p.m.

The germinated seed broth (800 ml) is inoculated into a 30-liter jar containing 20 liters of Medium S-1 and incubated for 64 hours at 28° C. with aeration of 20 liters per minute and under an internal pressure of 0.2–0.3 kg/cm² and stirring at 200 to 300 r.p.m.

(b) Isolation process

The fermentation broth of the above process is centrifuged by a Sharpless centrifugal separator. The supernatant fluid (122 liters) is cooled to 10° C., adjusted to pH 7.0 and passed through a column of 10 liters of Dowex 1×2 (Cl$^-$) (by Dow Chemical Co., USA) at a rate of 500 ml per minute. The column is eluted with a 5% sodium chloride-cooled deionized water solution. The fractions (18 liters) showing anti-bacerial activity as checked by the pulp disk diffusion method with *Escherichia coli* are collected, adjusted to pH 7.0, and passed through a column of 9 liters of Diaion HP-20 (by Mitsubishi Kasei Co.,) at a rate of 150 ml per minute. The column is eluted with cooled deionized water containing 2% methanol. The active fractions (9.6 liters) are collected, adjusted to pH 7.0 and lyophilized to give a crude powder (14.25 g).

(c) Purification process

The crude powder of PA-39504-$X_1$ (13.8 g) prepared above is dissolved in water (30 ml) and applied to a column of about 500 ml of Dowex AG 1×2 ($Cl^-$). The column is eluted with 0.005 M ammonium chloride (adjusted to pH 7.0 with ammonium hydroxide) and 0.4–3.0% sodium chloride solutions by gradient method. The eluates are separated into five fractions by checking the activity by pulp disk diffusion method with *Escherichia coli*. Each fraction is desalted with a column of Diaion HP-20, condensed and lyophilized. The crude powder (776 mg) obtained from the second fraction is dissolved in water (3 ml) and applied to a column of 120 ml of Dowex AG 1×2 ($Cl^-$). The column is eluted with 0.05–0.5 M phosphate buffer solution (pH 7.0) by gradient method. The active fraction is desalted in the same manner as noted above and lyophilized to give a powder (172 mg). The powder is dissolved in water (0.5 ml) and applied to a column of LiChroprep RP-18 (by Merck E. AG) (20 mm×50 cm). The column is eluted with 0.05 M phosphate buffer solution (pH 7.0). The active fractions are desalted and lyophilized to give a powder (60 mg).

The resultant powder (60 mg) is dissolved in 0.05 M phosphate buffer solution (pH 7.0) and applied to high performance liquid chromatography with a column (10 mm×30 cm) of Nucleosil-5-$C_{18}$ (M. Nargel Co., West Germany) with the above buffer solution as eluent. The active fraction desalted and lyophilized to give a powder (16 mg).

The powder (16 mg) is applied to high performance liquid chromatography on Nucleosil-5-$C_8$ (10 mm×30 cm) with 0.1 M phosphate buffer solution (pH 7.0), desalting and lyophilization to give an amorphous powder (1.5 mg) of PA-39504-$X_1$.

EXAMPLE 2

PA-39504-$X_1$ is obtained by using *Streptomyces tokunonensis* PA-31088 (FERM-P No. 4843) in the same manner as in Example 1.

What is claimed is:

1. A process for producing an antibiotic PA-39504-$X_1$ of the formula:

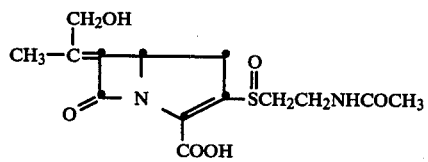

which comprises cultivating *Streptomyces argenteolus* PA-39504- or *Streptomyces tokunonensis* PA-31088, or a mutant or a variant thereof under aerobic conditions and isolating the accumulated antibiotic PA-39504-$X_1$ from the cultured broth.

2. The process claimed in claim 1, wherein *Streptomyces argenteolus* PA-39504 is cultivated.

3. The process claimed in claim 1, wherein *Streptomyces tokunonensis* PA-31088 is cultivated.

4. The process claimed in claim 1, wherein the cultivation is effected at about 20° to 40° C. for about 20 to 80 hours.

* * * * *